United States Patent [19]

Jiang

[11] Patent Number: 6,060,509
[45] Date of Patent: May 9, 2000

[54] ANTIFUNGAL AGENTS

[75] Inventor: Zhi-Dong Jiang, Burlington, Mass.

[73] Assignee: Millennium Pharmaceuticals, Inc., Cambridge, Mass.

[21] Appl. No.: 09/224,709

[22] Filed: Dec. 31, 1998

Related U.S. Application Data

[62] Division of application No. 08/674,896, Jul. 3, 1996, Pat. No. 5,917,084.

[51] Int. Cl.$^7$ .......................... C07C 31/00; C07C 31/215
[52] U.S. Cl. .......................... 514/510; 514/549; 514/623; 514/715; 514/729
[58] Field of Search ..................................... 514/510, 549, 514/623, 715, 729, 676, 691, 661, 706, 716

[56] References Cited

FOREIGN PATENT DOCUMENTS 0 505 135 A2   9/1992   European Pat. Off. .

OTHER PUBLICATIONS

Cottard et al., Synthesis of a . . . lejimalides, Tetrahedron Letters, vol. 36, No. 18, pp. 3115–3118 (1995) Month not provided.

White et al., Synthesis of . . . Coupling Strategy, Tetrahedron, vol. 51, No. 20, pp. 5743–5756 (1995) Month not provided.

Bohlmann et al., "Neue Eremophilene Aus Südafrikanischen Senecio–Arten", Phytochem., 17:1337–41 (1978) Month not provided.

Neunschwander et al., "63, Struktur der Sequiterpene von Petasites hybridus (L.) G.M. et SCH.: Petasol–und Isopetasol–Abkömmlinge," Helvetica Chimca Acta, 62:609–634 (1979) No month provided.

Yamakawa et al., "Steroselective Total Synthesis of (±)–Eremofortin B, A Sesquiterpenoid Mycotoxin of Penicillium roqueforti," Chem. Letters, The Chem. Soc. of Japan, pp. 929–932 (1981) No month provided.

Tirilly et al., "A Fungitoxic Sesquiterpene from Hansfordia Pulvin ATA," Phytochem., 22(9):2082–83 (1983) No month provided.

Kim et al., "A Brassinolide–Inhibitor KM–01, Its Isolation and Structure Elucidation from a Fungas Drechslera avenae," Tetrahedron Letters, 35(11):1731–1734 (1994) No month provided.

Yoshizawa et al., "Incorporation of $^{13}$C–Labelled 5–epi–A-ristolochene into Capsidiol in Green Pepper Seedlings," Biosci. Biotech. Biochem., 58(2)305–308 (1994).

Abstracts, Dictionary of Natural Products on CD–ROM, Release 3:2, pp. 1–8 (1995) No month provided.

Kim et al., "Biological Activity of Brassinosteroid Inhibitor KM–01 Produced by a Fungus Drechslera avenae," Biosci. Biotech. Biochem., 59(8)1394–1397 (1995) No month provided.

Witschel et al., Synthese der Pestwurzinhaltsstoffe (+)–Petasin und (+)–Isopetasin, Tetrahedron Letters, 36(19):3325–3328 (1995) No month provided.

*Primary Examiner*—Johann Richter
*Assistant Examiner*—Rosalynd Keys
*Attorney, Agent, or Firm*—Fish & Richardson P.C.

[57] ABSTRACT

A pine root (*Deutero mycetes*) fungal metabolite and analogs thereof having antifungal activity.

5 Claims, No Drawings

ANTIFUNGAL AGENTS

CROSS REFERENCE TO RELATED APPLICATIONS

This application is a divisional of application Ser. No. 08/674,896 filed Jul. 3, 1996 which is now U.S. Pat. No. 5,917,084.

A related application was co-filed with this application on Jul. 3, 1996, attorney docket No. 06286/022001, which is application Ser. No. 08/674,829, now U.S. Pat. No. 5,932,613.

BACKGROUND OF THE INVENTION

The invention relates to naturally occurring terpenoid compounds and derivatives or analogs thereof having antifungal activity.

SUMMARY OF THE INVENTION

In general, the invention features a compound having the formula (I):

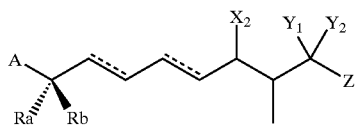

(I)

In formula (I), A is $C_{2-10}$ 1-methylalkyl, 1-($C_{1-10}$ alkyloxy)ethyl, 1-($C_{1-10}$ alkylthio)ethyl, $C_{2-10}$ hydroxycarbonylalkyl, $C_{2-10}$ alkenyl, $C_2$ alkenylene, $X_1(CH-)R_1$, or $X_1(C-)R_1$, wherein $X_1$ is H, F, Cl, Br, I, $C_{1-10}$ alkyl, $C_{2-10}$ alkenyl, $C_{2-10}$ alkenylene (where A is $X_1(C-)R_1$), $C_{1-10}$ haloalkyl, $OR_i$, $SR_i$, $NR_iR_{ii}$, or $NR_i(C=O)R_{ii}$, each of $R_i$ and $R_{ii}$ being independently selected from H, $C_{1-10}$ alkyl, $C_{3-6}$ heteroaryl, and ($C_{6-14}$ aryl) ($C_{0-6}$ alkyl); and $R_1$ is H or methyl, or =O where A is $X_1(C-)R_1$. Each of $R_a$ and $R_b$ is selected independently from H, $C_{1-6}$ alkyl, $C_{1-6}$ haloalkyl, and $C_{1-6}$ alkenyl, except that where A is $C_{2-10}$ alkenylene, $R_b$ is deleted. $X_2$ is H, F, Cl, Br, I, $NO_3$, $SO_4$, $C_{1-10}$ alkyl, $C_{1-10}$ haloalkyl, $OR_{iii}$, $O(C=O)R_{iii}$, $SR_{iii}$, $NR_{iii}R_{iv}$, or $NR_{iii}(C=O)R_{iv}$, wherein each of $R_{iii}$ and $R_{iv}$ is independently selected from H, $C_{1-10}$ alkyl, and ($C_{6-14}$ aryl) ($C_{0-6}$ alkyl). Each of $Y_1$ and $Y_2$ is independently selected from H, $C_{1-10}$ alkyl, $OR_v$, $SR_v$, $NR_vR_{vi}$, and $NR_v(C=O)R_{vi}$, wherein each of $R_v$ and $R_{vi}$ is independently selected from H, $C_{1-10}$ alkyl, and ($C_{6-14}$ aryl) ($C_{0-6}$ alkyl); or $Y_1$ and $Y_2$, taken together, are =O, =S, =$NR_{vii}$, =$NOR_{vii}$, or =$CHR_{vii}$ in the E or Z configuration, wherein $R_{vii}$ is H, $C_{1-10}$ alkyl, ($C_{6-14}$aryl)-($C_{0-10}$alkyl), or ($C_{1-10}$ alkyl) ($C_{6-14}$ aryl). Z is H, $C_{1-10}$ alkyl, $C_{2-10}$ alkenyl, or a monovalent $C_{1-30}$ organic moiety, said moiety being bonded to the carbon which is also bonded to $Y_1$ and $Y_2$ by a heteroatom selected from O, S, and N. The invention also features pharmaceutically acceptable salts or esters of formula (I)

Compounds of the invention include, for example, the compound 3390, and synthetic intermediates of the disclosed compounds, such formulae (II) and (III). The invention also features methods of making the disclosed compounds.

The invention also features compounds having the formula (VI):

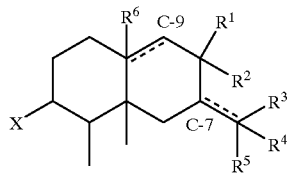

(VI)

Each of $R^1$ and $R^2$ is independently selected from H, $C_{1-10}$ alkyl, $C_{1-10}$ alkoxy, $C_{2-10}$ alkenyl, $C_{2-10}$ alkenoxy, $C_{6-10}$ aryl, substituted or unsubstituted $C_{6-10}$ arylcarbonyloxy, and $C_{2-10}$ acyloxy; or $R^1$ and $R^2$ taken together are =O or substituted or unsubstituted $C_{1-10}$ alkylenedioxy, carbonyldioxy, and other carbonyl-protecting groups. When there is no double bond between C-7 and C-11, each of $R^3$, $R^4$ and $R^5$ is independently selected from $C_{1-10}$ alkyl, $C_{1-10}$ alkoxy, and $C_{1-10}$ acyloxy; or $R^4$ and $R^5$ taken together are =O, $C_{1-10}$ alkylidene, or $C_{1-10}$ alkenylidene. When there is a double bond between C-7 and C-11, $R^5$ is absent. $R^6$ is $C_{1-10}$ alkylamino or $C_{1-10}$ alkylthio when there is no double bond between C-9 and C-10; $R^6$ is absent when there is a double bond between C-9 and C-10. X is H, OH, $OR_p$ where $R_p$ is $C_{1-10}$ alkyl, $C_{6-10}$ aryl, $C_{2-10}$ acyl, $C_{6-10}$ arylcarbonyl, tri($C_{1-6}$ alkyl)silyl, and other hydroxy-protecting groups, or Y having the formula:

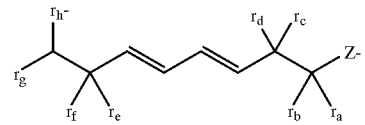

Z is —(C=O)—NH—, —(C=O)—O—, —O—, —NH—(C=O)—, or —O—(C=O)—. Each of $r_a$–$r_h$ is independently selected from H, methyl, halomethyl, hydroxy, and $OR_p$, where $R_p$ is $C_{1-10}$ alkyl, $C_{6-10}$ aryl, $C_{2-10}$ acyl, $C_{6-10}$ arylcarbonyl, and other hydroxy-protecting groups, provided that at least two of $r_a$–$r_h$ are hydroxyl groups which do not form a gem-diol. Additional limitations are: where X is OH, —C($R^3$) ($R^4$) ($R^5$) is neither isopropenyl nor isopropylidene; where X is O-(trialkylsilyl), —C($R^3$) ($R^4$) ($R^5$) is not 2-hydroxylisopropyl; and provided that when $R^1$ $R^2$, and X are H, —C($R^3$) ($R^4$) ($R^5$) is not isopropenyl; or a pharmaceutically acceptable salt or ester thereof.

In another aspect, the invention features a method of treating a fungal infection in a human patient by administering an effective amount of a pharmaceutical composition containing one or more compounds of the invention to the patient, thereby inhibiting the growth of fungal infection in the patient. Treating a fungal infection includes achieving one or more of the following, partially or substantially: reducing fungal load in an affected tissue or organ, inhibiting fungal growth, arresting fungal growth, decreasing production of harmful fungal metabolites, and ameliorating clinical symptoms or indicators (e.g., tissue or serum) associated with fungal infection. An antifungal agent may therefore be fungicidal or fungistatic.

Other features and advantages of the present invention will be apparent from the following detailed description, and also from the appended claims.

DETAILED DESCRIPTION OF THE INVENTION

A. Abbreviations

AIBN, 2,2'-azobis(isobutyronitrile); DCC, dicyclohexylcarbodiimide; DMAP, dimethylaminopyridine; HOBT, 1-hydroxybenzotriazole hydrate; PMB, p-methoxybenzyl; DMF, dimethylformamide; MS, methanesulfonyl; Tf, trifluoromethanesulfonyl; and Perkin (AIBN, RSH).

B. Terms

Acetogenins are naturally derived from polyketones having a β-dicarbonyl structure. Examples of acetogenins which contain at least one hydroxyl group include chrysin, protocoin, emodin, atrovenetin, visamminol, alternariol, and α-sorigenin.

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyano, methylsulfonylamino, alkoxy, acyloxy, nitro, and lower haloalkyl. Similarly, cycloalkyl, aryl (e.g., phenyl, naphthyl, biphenylyl, 2,4-dihalophenyl, 2,6-dihalophenyl), arylalkyl (e.g., benzyl), alkylaryl (e.g., 2,4-dimethylphenyl), heteroaryl, and heterocyclic radical groups may be subsituted with one or more of the above substituting groups. Examples of cycloalkyl groups are cyclopropyl, cyclobutyl, cyclopentyl, cyclohexyl, cycloheptyl, and cyclooctyl.

An alkylene is a bivalent radical derived from alkanes by removing two hydrogens from two different carbon atoms. Examples of alkylenes include —$CH_2$—CH(R)—$CH_2$ and 1,4-cyclohexylene. An alkylidene is a bivalent radical derived from alkenes by removing two hydrogens from the same carbon atom, such as 1-propanyl-3-ylidene (=CH—$CH_2$—$CH_2$—).

Unless otherwise indicated, complex moieties such as arylalkyl or alkylcarbonyloxy groups are bonded to the rest of the molecule via the last-named radical moiety, in these examples, alkyl and oxy, respectively. Exceptions include moieties such as $X_1$(CH—)$R_1$ and $X_1$(C—)$R_1$, which are bonded to the rest of the molecule via the central carbon atom, as indicated by the radical-indicating convention "—". Thus, in the former case, the central carbon atom C is bonded to H, $X_1$, $R_1$, and finally the carbon atom which is also bonded to $R_a$ and $R_b$ as shown in formula (I).

An aryl group is a $C_{6-20}$ aromatic ring, wherein the ring is made of carbon atoms (e.g., $C_{6-14}$, $C_{61-10}$ aryl groups). Examples of haloalkyl include fluoromethyl, dichloromethyl, trifluoromethyl, 1,1-difluoroethyl, and 2,2-dibromoethyl.

A dehydro moiety of a $C_{1-30}$ organic compound (e.g., a natural product) is the organic compound with a hydrogen atom removed. The removed hydrogen leaves a single valence on a carbon, nitrogen, oxygen, sulfur, or silicon atom of the organic compound. The dehydro moiety is bonded to a compound disclosed herein via the single valence. Examples include (i) natural products selected from the group consisting of monoterpenes, diterpenes, sesquiterpenes, steroids, and polyketides; and (ii) naturally occurring amino acids.

A heterocyclic radical contains at least one ring structure which contains carbon atoms and at least one heteroatom (e.g., N, O, S, or P). A heteroaryl is an aromatic heterocyclic radical. Examples of heterocyclic radicals and heteroaryl groups include: thiazolyl, thienyl, thiophenyl, furyl, 1-isobenzofuranyl, 2H-chromen-3-yl, 2H-pyrrolyl, N-pyrrolyl, imidazolyl, pyrazolyl, isothiazolyl, isooxazolyl, pyridyl, pyrazinyl, pyrimidinyl, pyradazinyl, indolizinyl, isoindolyl, indolyl, indazolyl, purinyl, phthalazinyl, cinnolinyl, and pteridinyl. A heterocylic radical or heteroaryl may be attached to another moiety via a carbon atom or a heteroatom of the radical.

A ($C_n$ alkyl)oxycarbonyl group has the formula R—O—(C=O)—. For example, ($C_{1-6}$ alkyl)oxycarbonyl, therefore, includes methoxycarbonyl and hexyloxycarbonyl. A $C_{1-10}$ acyl group as used herein is of the formula —(C=O)—$L_3$ and contains 1 to 10 carbon atoms and 1–5 heteratoms. Examples of such acyl groups include formyl, acetyl, benzyloxycarbonyl, tert-butoxycarbonyl, trifluoroethyloxycarbonyl, thiobenzoyl, phenylamidocarbonyl, and 4-nitrophenoxycarbonyl.

Polyketides are a class of chemicals including linear polyketides, marine halogenated acetogenins, annonaceae acetogenins, macrolide polyketides, lactone polyketides, ansamycins, polyenes, linear tetracyclines, angucyclines, polyether antibiotics, and aflatoxins.

A salt is an ionic derivative of a compound of the invention wherein a hydrogen atom is removed (e.g., deprotonation of a carboxylic acid to form a carboxylate anion) or a hydrogen atom is added (e.g., protonation of an amino group to form an ammonium cation), and one or more suitable counterions are added. Counterions may be organic or inorganic, and are, in general, biologically acceptable (e.g., pharmaceutically or agriculturally acceptable). Examples of counter-cations include primary, secondary, or tertiary ammoniums or organic amines, group IA alkaline metal ions, and group IIA alkaline earth metal ions. Examples of counter-anions include halogen, nitrate, sulfate, citrate, salicylate, acetate, succinate, and acetylsalicylate. In certain embodiments, salts are formed by reacting a carboxylic acid- or amine-containing compound of the invention with hydrogen bromide, hydrogen chloride, or trifluoroacetic acid.

Unless otherwise indicated, in the structures provided herein, double bonds between $r_1$ and $r_2$, and $r_3$ and $r_4$, may be present (cis or trans, preferably trans) or absent (e.g., hydrogenated, alkylated, or halogenated). According to convention, a structure drawn with single, uniform lines includes both the (R) and (S) stereoisomers of any chiral carbon atom. Unless otherwise indicated, the compounds of the invention include both the (R) and (S) forms, although in certain embodiments it may be desirable to separate the various stereoisomers due to differences in activity. Such resolution is accomplished by means known to those skilled in asymmetric synthesis and chiral separation (e.g., chromatography).

Steroids include aromatic ring A $C_{18}$ estrane, $C_{19}$ androstanes, $C_{20}$ 19-norpregranes, $C_{21}$ pregnanes, $C_{23}$ 24-norcholan-23-oic-acid steroids, cardanolide steroids ($C_{23}$), cholan-24-oic acid steroids ($C_{24}$), other cholane steroids ($C_{24}$), bufanolide steroids ($C_{24}$), homocholane steroids (26,27-dinorcholestanes) ($C_{25}$), 27-norcholestane steroids ($C_{26}$), neutral cholestane steroids ($C_{27}$), cholestanoic acid steroids ($C_{27}$), ecdysteroids ($C_{27}$), spirostan steroids ($C_{27}$), furostan steroids ($C_{27}$), ergostane steroids (excluding withanolides and brassinolides) ($C_{28}$), withanolide and brassinolide steroids ($C_{28}$), stigmastane steroids ($C_{29}$), gorgostane and other cyclopropacholestane steroids ($C_{30}$), vitamin $D_3$ (cholecalciferol) metabolites and analogues, and vitamin $D_2$ (ergocalciferol) metabolites and analogues.

Terpenes are natural plant products having a multiple of five carbon atoms. Skeletal types of monoterpenes contain 10 carbon atoms and are acyclic (e.g., myrcane, artemisane, santolinane, lavandulane, secoiridane, senecic acid, and incanic acid), monocyclic (e.g., eucarbone, α-thujaplicin, p-menthane, o-menthane, m-menthane, cyclogeraniolane, β-cyclolavandulal, ferulol, chondrocole, cantharidin, α-campholene aldehyde, polyzonimine, fragranol, junioine, and chrysanthemane), bicyclic or tricyclic (e.g., thujane, carane, pinane, bornane, isocamphane, fenchene, photocitral, filifolone, or tricyclene). Specific examples include geraniol, myrcene, menthol, α-pinene, and camphene. See, also, *CRC Handbook of Terpenoids,* ed. Sukh Dev (1982) vols. I and II.

Sesquiterpenes are $C_{15}$ compounds. Skeletal types include mono- and bicyclofarnesane, trans,trans-farnesyl diphosphate, nerolidyl diphosphate, cis,trans-farnesyl diphosphate, farnesane, bicyclogermacrane, maaliane, aristolane, aromadendrane, germacrane, eudesmane, guaiane, elemane, elemophilane, valencane, valerane, humulane, caryophyllane, proto-illudane, illudane, hirsutane, marasmane, bisabolane, santalene, bergamotane, acorane, cedrane, chamigrane, thujopsane, widdrane, cuparane, laurane, trichothecane, cadinane, amorphane, muurolane, bulgarane, sativane, copaane, cubebane, ylangane, himachalane, longifolane, longibornane, longipinane. furamoid farnesane sesquiterpenoids, irregular acyclic sesquiterpenoids, miscellaneous cyclobutane sesquiterpenoids, cyclopentane sesquiterpenoids, cyclofarnesane sesquiterpenoids, rearranged cyclofarnesane sesquiterpenoids, bisabolane sesquiterpenoids, miscellaneous cyclohexane sesquiterpenoids, cycloheptane sesquiterpenoids, cyclobisabolane sesquiterpenoids, elemane sesquiterpenoids, simple germacrane sesquiterpenoids, 12,6-germacranolide sesquiterpenoids, 12,8-germacranolides and furanogermacrane sesquiterpenoids, nor- and homogermacrane sesquiterpenoids, secogermacrane sesquiterpenoids, cyclogermacrane sesquiterpenoids, lepidozanes and bicyclogermacrane sesquiterpenoids, humulane sesquiterpenoids, caryophyllane sesquiterpenoids, bicyclohumulane sesquiterpenoids, cuparane sesquiterpenoids, syslolaurane sesquiterpenoids, herbertane sesquiterpenoids, laurane sesquiterpenoids, trichothecane sesquiterpenoids, simple eudesmane sesquiterpenoids, 12,6-eudesmanolide sesquiterpenoids, 12,8-eudesmanolides and furanoeudesmane sesquiterpenoids, agarofuran eudesmane sesquiterpenoids, secoeudesmane sesquiterpenoids, noreudesmane sesquiterpenoids, emmotin sesquiterpenoids, oppositane sesquiterpenoids, farfugin sesquiterpenoids, cycloeudesmane sesquiterpenoids, gorgonane sesquiterpenoids, simple eremophilane sesquiterpenoids, eremophilanolide and furanoeremophilane sesquiterpenoids, seco- and abeoeremophilane sesquiterpenoids, noreremophilane sesquiterpenoids, chiloscyphane sesquiterpenoids, aristolane sesquiterpenoids, nardosinane sesquiterpenoids, brasilane sesquiterpenoids, cacalol sesquiterpenoids, valerane sesquiterpenoids, miscellaneous rearranged eudesmane sesquiterpenoids, cadinane sesquiterpenoids, nor- and secocadinane sesquiterpenoids, alliacane sesqui-terpenoids, oplopane sesquiterpenoids, mutisianthol sesquiterpenoids, drimane sesquiterpenoids, coloratane sesquiterpenoids, nor- and secodrimane sesquiterpenoids, xanthane sesquiterpenoids, carabrane sesquiterpenoids, simple guaiane sesquiterpenoids, 12,6-guaianolide sesquiterpenoids, 12,8-guaianolide, dimeric guaiane sesquiterpenoids, seco-, cyclo-, abeo-, and norguaiane sesquiterpenoids, pseudoguaiane sesquiterpenoids, seco-, cyclo-, abeo and norpseudoguaiane sesquiterpenoids, aromadendrane sesquiterpenoids, cycloaromadendrane sesquiterpenoids, secoaromadendrane sesquiterpenoids, cubebane sesquiterpenoids, ivaxillarane sesquiterpenoids, patchoulane sesquiterpenoids, rearranged patchoulane sesquiterpenoids, valerenane sesquiterpenoids, africanane sesquiterpenoids, himachalane sesquiterpenoids, longipinane sesquiterpenoids, longifolane sesquiterpenoids, pinguisane sesquiterpenoids, thapsane sesquiterpenoids, fukinane sesquiterpenoids, picrotoxane sesquiterpenoids, daucane sesquiterpenoids, isodaucane sesquiterpenoids, perforane sesquiterpenoids, pacifigorgiane sesquiterpenoids, asteriscane sesquiterpenoids, illudane sesquiterpenoids, protoilludane sesquiterpenoids, sterpurane sesquiterpenoids, illudalane sesquiterpenoids, isolactarane sesquiterpenoids, lactaran sesquiterpenoids, marasmane sesquiterpenoids, furodysin sesquiterpenoids, furodysinin sesquiterpenoids, botrydial sesquiterpenoids, spriovetivane sesquiterpenoids, acorane sesquiterpenoids, chamigrane sesquiterpenoids, secochamigrane sesquiterpenoids, miscellaneous spirosesquiterpenoids, cedrane sesquiterpenoids, isocedrane sesquiterpenoids, zizaane sesquiterpenoids, prezizaane sesquiterpenoids, clovane sesquiterpenoids, precapnellane sesquiterpenoids, capnellane sesquiterpenoids, hirsutane sesquiterpenoids, rearranged hirsutane sesquiterpenoids, pentalenane sesquiterpenoids, silphinane sesquiterpenoids, silphiperfoliane sesquiterpenoids, presilphiperfoliane sesquiterpenoids, isocomane sesquiterpenoids, panasinsane sesquiterpenoids, modhephane sesquiterpenoids, quadrane sesquiterpenoids, campherenane sesquiterpenoids, α-santalane sesquiterpenoids, β-santalane sesquiterpenoids, sativane sesquiterpenoids, copacamphane sesquiterpenoids, sinularane sesquiterpenoids, capaane sesquiterpenoids, ishwarane sesquiterpenoids, rotundane sesquiterpenoids, thujopsane sesquiterpenoids, bourbonane sesquiterpenoids, gymnomitrane sesquiterpenoids. Specific examples include farnesol, bisabolene, α-cadinol, and hinesol. Eremophilanes include 3-hydroxy-9,11-eremophiladien-8-one (e.g., 3α,7α-form, and 3α,7β-form); 3,12-dihydroxy-9,11,(13)-eremophiladien-8-one (3α,7βH-form); eremofortin B; 9,11-eremophiladien-8-one; 6α,7α-epoxy-3α,13-dihydroxy,-9,12-eremophiladien-9-one; 13-desoxyphomenone, phaseolinone, phomenone, 1,3-dihydroxy-9,11-eremophiladien-8-one (1α,3α,7βH-form), petasin, S-petasin, isopetasin, iso-S-petasin, petasol, and isopetasol.

Diterpenes are $C_{20}$ compounds biogenetically derived from geranylgeranyl pyrophosphate, and include resin acids and gibberellins. Examples of diterpenoid skeletons include irregular linear diterpenoids, linear homo- and nor-diterpenoids, prenylbisabolane, 10,15-cyclophytane, labdane, secolabdane, norlabdane, halimane, rearranged labdane, colesane, clerodane, nor-, seco- and abeoclerodane, abietane, furanoabietane, furanoabietane, secoabietanes and secofriedoabietane, nor- and homoabietane, abeoabietane, dimeric abietane, 13,16-cycloabietane, 17(15→16) abeoabietane, totarane, nagilactone, pimarane, rosane, erythroxylane, paraguarane, devadarane, isopimarane, rearranged pimarane and isopimarane, norpimarane and morisopimarane, cassane, vouacapane, cleistanthane and isocleistanthane, isolane and spongiane, seco-, nor- and abeospongiane, podocarpane, kaurane, phyllocladane, norkaurane, secokaurane, rearranged kaurane, beyerane, nor- and secobeyerane, villanovane, atisane, trachylobane, helifulvane, aphidicolane, gibberellins, rearranged gibberellins, leucothol, grayanotoxane, cembrane, norcembrane, rearranged cembrane, eunicellane, asbestinane, sphaerane, briarane, dolabellane, modified dolabellane, dolastane, modified dolastane, cyathane, sphaeroane, verrucosane, modified verrucosane, casbane, jatrophane, 9,13-cyclojatrophane, lathyrane, rhamnofolane, daphnane, tigliane, ingenane, jatropholane and secojatropholane, fusicoccane, valparane, spatane, seco- and abeospatane, verticillane, taxane, trinervitane, kempane, amphilectane, cycloamphilectane, adociane, xenicane, nor-, seco- and cycloxenicane, phyllane, viscidane, eremane, prenyleudesmane, prenylgermacrane, prenylbicyclogermacrane, lobane, prenylguaiane, cneorubine, serrulatane and biflorane, decipiane, sacculatane, obtusane, irieol, sphenolobane, geranylgeraniol, beyerane, and gibberllane. Specific diterpenes include geranylgeraniol and dextropimaric acid.

Triterpenes are $C_{30}$ compounds. Examples of triterpene skeletal structures include linear triterpenoids, botryococcenes, protostanes, fusidanes, lanostanes, cycloartane, cucurbitane, dammarane, triucallane/euphane, apotirucallane, intact tetranortriterpenoids, ring cleaved tetranortriterpenoids, rearranged tetranortriterpenoids, quassinoid nortriterpenoids, baccharane, lupane, 3(2→1) abeolupane, nor- friedo- and secolupane, oleanane, nor-, seco- and abeooleanane, taraxerane, nor-, seco- and cyclotaraxerane, multiflorane, glutinane, friedelane, nor- and secofriedelane, pachysanane, taraxastane, ursane, nor-, seco- and abeoursane, bauerane, hopane, nor- seco, and abeohopane, neohopane, fernane, squalene, onocerane, serratane, ambrane, malabaricane, gammacerane, protostane, lanostane, cycloartane, arborane, hopane, fernane, filicane, dammarane, apo-euphane, euphane, shionane, germanicane, taraxsterane, and phyllanthane.

C. Natural product isolation

1. Extraction

The supernatant (7 L) from a pine root (Deutero myeates) fungal culture was extracted with about an equal volume of ethyl acetate (6–10 L). The ethyl acetate extract was concentrated by rotary evaporation under vacuum at 32° C. to yield between 1.0 and 2.5 g green syrup from the supernatant. The mycelium was extracted with 3 L methanol; methanol filtrate was concentrated by rotary evaporation under vacuum at 32° C. to yield about 1 L aqueous solution. Extraction with an equal volume of ethyl acetate and concentration as above yielded material which was combined with the supernatant extract.

The combined extracts were separated on a C-18 (EK Science, Gibbstown, N.J.) 40–63 μm column 4.5 cm h×3.5 cm diameter. After eluting with a step gradient of methanol/water (50%, 75%, 85%, and 100%, 250 ml each step), [*volume*] fraction were analzyed an silica gel TLC precoated with Kieselgel 60 F254 on aluminum sheet (EM Separations). The plates were developed with 60% ethyl acetate/hexanes and visualized with p-anisaldehyde. After concentrating the fraction containing compound 3390A in 75% methanol/water at 32° C. under vacuum, the resulting residue was separated by a silica gel 60 (EM Science, <0.063 mm) column 5.0 cm high×1.5 cm diameter, eluting with a step gradient of ethyl acetate/hexanes (25%, 50%, 75%, and 100%, 20 ml for each step). Both the 75% ethyl acetate/hexanes fraction and the 100% ethyl acetate fraction contained compound 3390. After combining these fractions, and purification by eluting with a step gradient of methanol/water through a C-18 (EM Science 40–63 μm) column 5.0 cm high×1.5 cm diameter yielded 7 mg of pure compound in the 80% methanol/water fraction.

2. Structural characterization

Compound 3390 showed a $UV_{max}$ at 231 nm ($\epsilon$=16,340 in methanol), indicative of a conjugated diene. Electrospray mass spectroscopy gave a $[M+Na]^+$ ion at m/z 453 in positive mode. Lithium chloride exchange gave a $[M+Li]^+$ ion at m/z 437, suggesting a molecular weight of 430. Proton and $^{13}C$ NMR signals were assigned (Table 1).

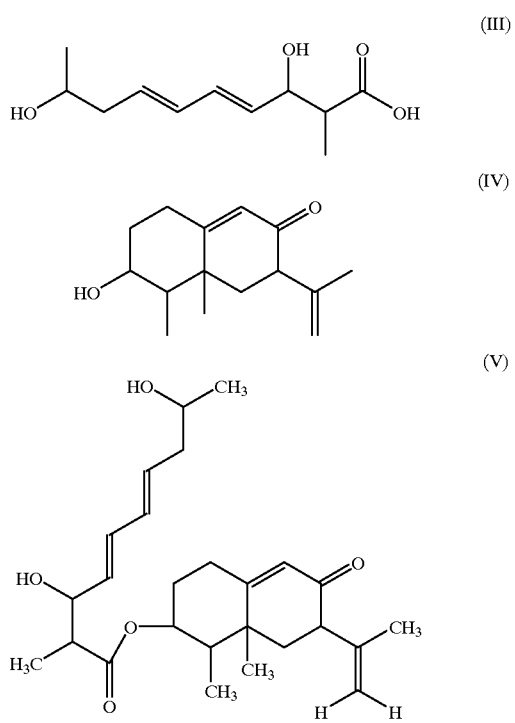

TABLE 1

| Carbon # | $^1H(\delta)$ (multiplicity, J in Hz) | $^{13}C(\delta)$ |
|---|---|---|
| 1 | 2.40 (ddd, 15.0, 3.5, 3.0) | 31.7 |
|  | 2.60 (ddd, 15.0, 5.0, 1.0) |  |
| 2 | 2.17 (m) | 32.8 |
|  | 1.49 (m) |  |
| 3 | 4.93 (m) | 74.9 |
| 4 | 1.64 (dq, 7.5, 7.0) | 48.6 |
| 5 |  | 41.5 |
| 6 | 1.94 (dd, 15.0, 14.5) | 43.1 |
|  | 2.05 (dd, 15.0, 5.0) |  |
| 7 | 3.22 (dd, 10.0, 4.5) | 51.6 |
| 8 |  | 201.3 |
| 9 | 5.76 (br. s) | 125.2 |
| 10 |  | 170.3 |
| 11 |  | 144.9 |
| 12 | 4.82 (br. s) | 115.0 |
|  | 4.93 (br. s) |  |
| 13 | 1.71 (s) | 20.4 |
| 14 | 0.98 (d, 6.5) | 10.9 |
| 15 | 1.27 (s) | 17.5 |
| 1' |  | 176.3 |
| 2' | 2.52 (m) | 48.0 |
| 3' | 4.21 (t, 8.0) | 75.7 |
| 4' | 5.54 (dd, 15.0, 8.0) | 132.4 |
| 5' | 6.24 (dd, 15.0, 10.5) | 134.0 |
| 6' | 6.11 (dd, 15.0, 10.5) | 133.1 |
| 7' | 5.74 (m) | 132.7 |
| 8' | 2.20 (m) | 43.5 |
|  | 2.25 (m) |  |
| 9' | 3.77 (h, 6.0) | 68.5 |
| 10' | 1.14 (d, 6.0) | 23.2 |
| 11' | 1.07 (d, 7.0) | 14.0 |

D. Synthesis

1. Semisynthesis

Representative derivatizations of the isolated natural product (compound 3390) are presented below. Semisynthetic methods concerning the generally linear portion of compound 3390 containing a conjugated diene, and the ring-containing or sesquiterpene portion of compound 3390. It will be easily apparent to one skilled in organic synthesis that the following transformations may be operated, in general, upon either the ester compound 3390 itself or upon the individually resolved alcohol and carboxylic acid hydrolysis products of the ester parent compound.

Derivatization of the hydroxyl group includes alkylation, reduction, oxidation, esterification, and silylation. Derivatization of the carboxylic acid group includes forming both esters and amides. A naturally-occurring amino acid includes the 20 common α-amino acids (Gly, Ala, Val, Leu, Ile, Ser, Thr, Asp, Asn, Lys, Glu, Gln, Arg, His, Phe, Cys, Trp, Tyr, Met and Pro), and other amino acids that are natural products, such as norleucine, ethylglycine, ornithine, methylbutenylmethylthreonine, and phenylglycine. Examples of amino acid side chains include H (glycine), methyl (alanine), —($CH_2$—(C═O)—$NH_2$ (asparagine), —$CH_2$—SH (cysteine), and —CH(OH)$CH_3$ (threonine).

Regarding the sesquiterpenoid portion, a wide variety of carboxylic acids or activated acyl groups can be reacted to form esters. $RCO_2H$, wherein R is alkyl, cycloalkyl, arylalkyl, branched arylalkyl, alkyl, amino acid esters with N-protection such as RO(C═O)NH— and R—(C═O)—NH—. The extracyclic vinyl and enone groups can also be derivatized. These and other transformations are provided in the following schemes.

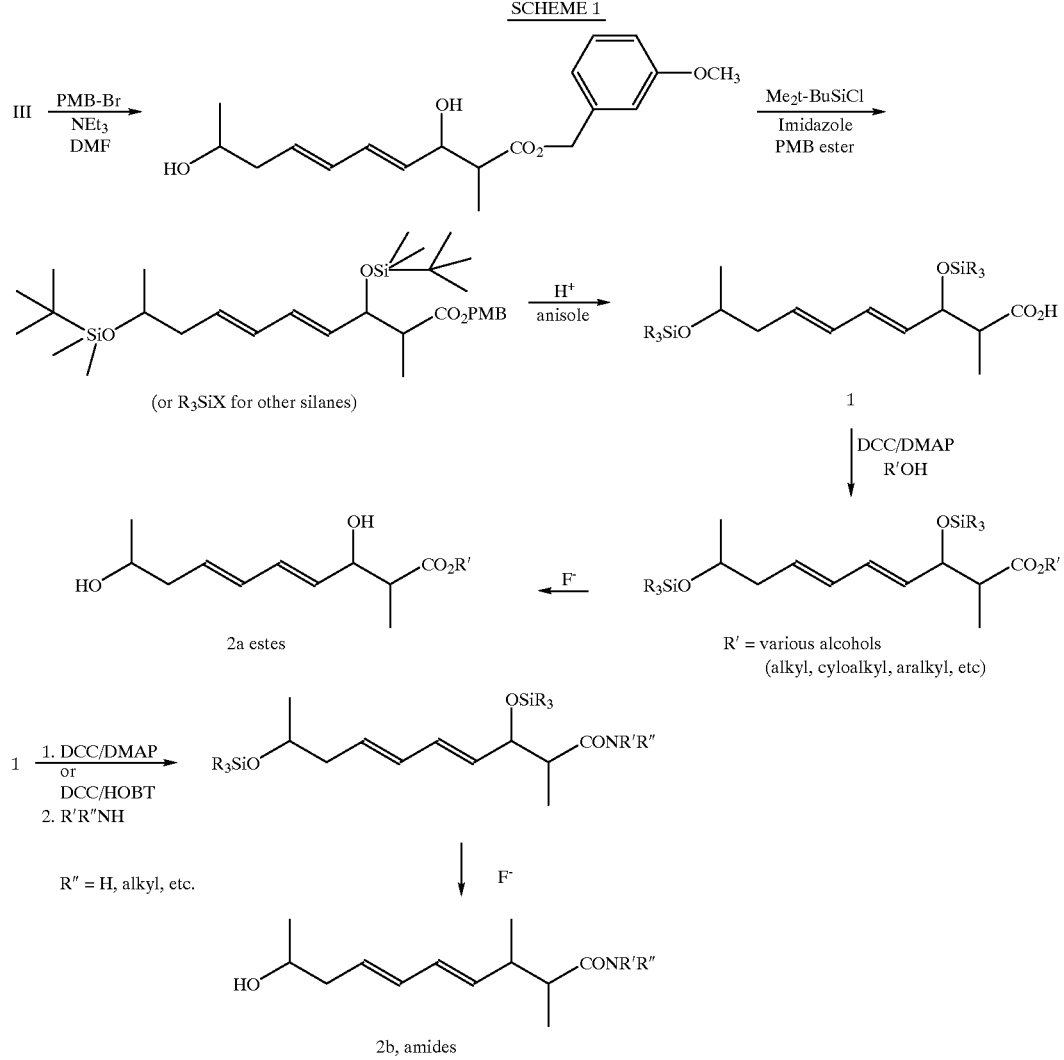

SCHEME 1

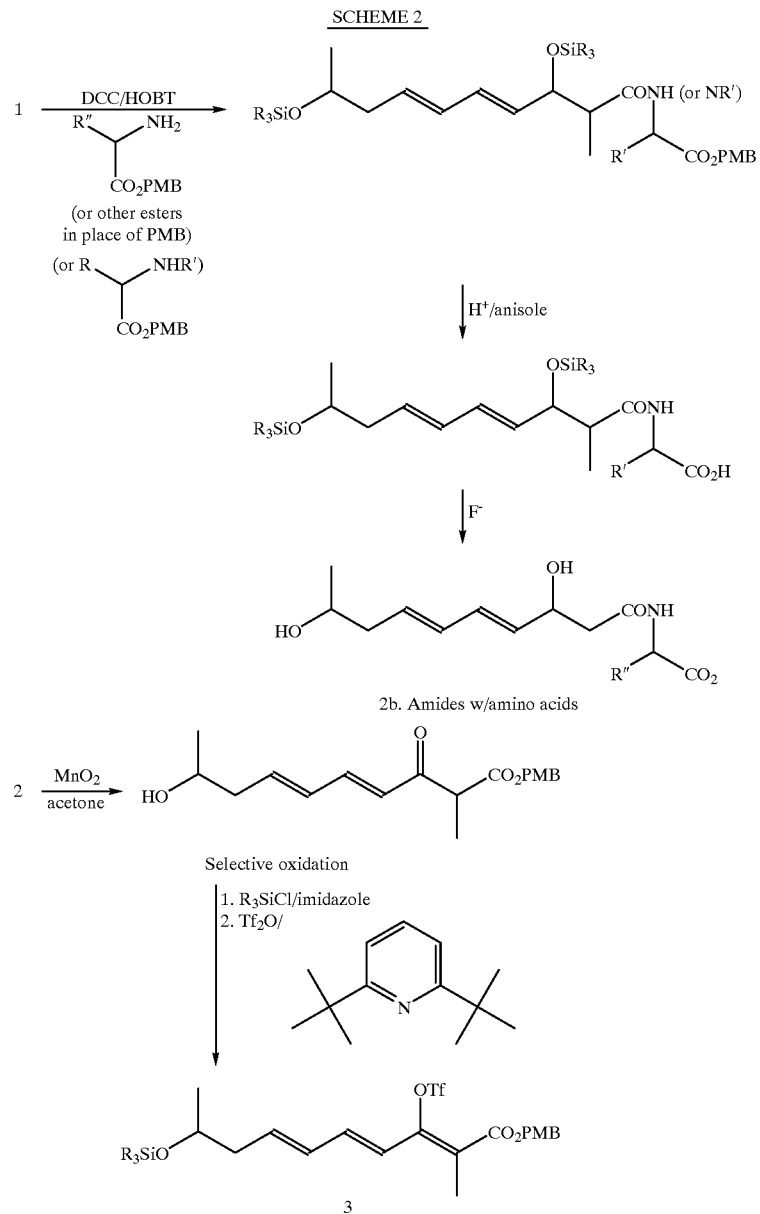
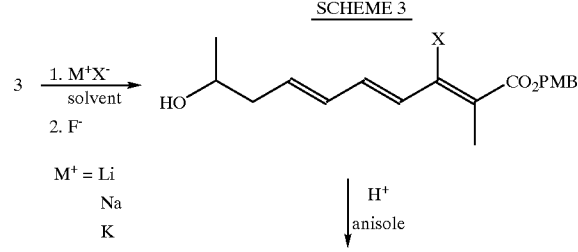

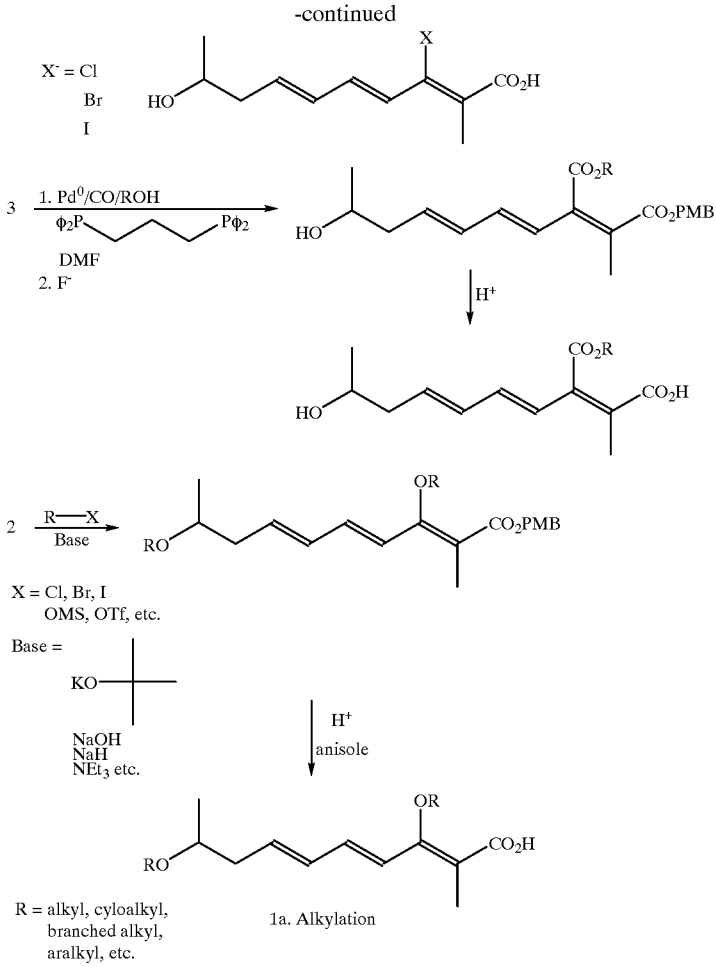
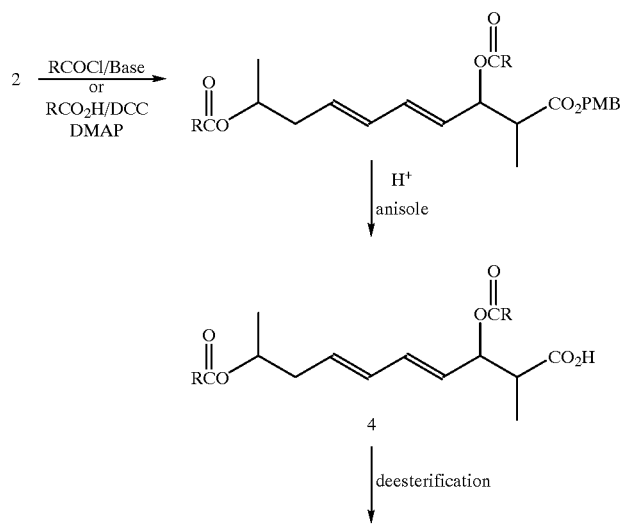
SCHEME 4

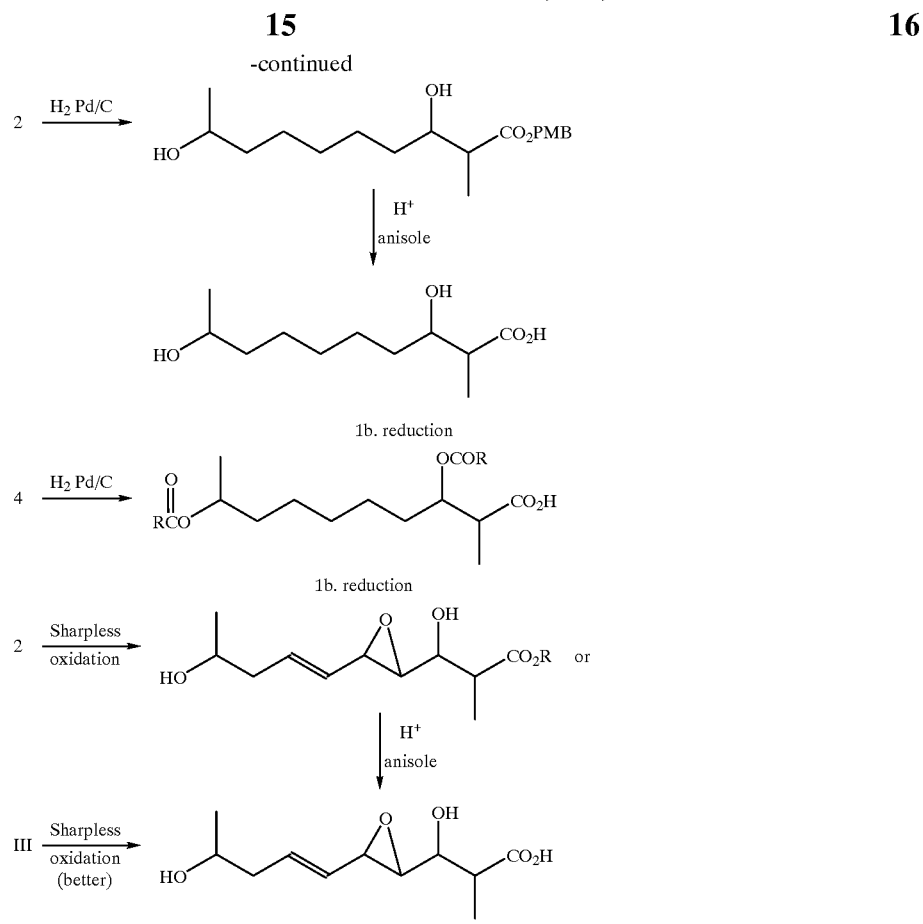
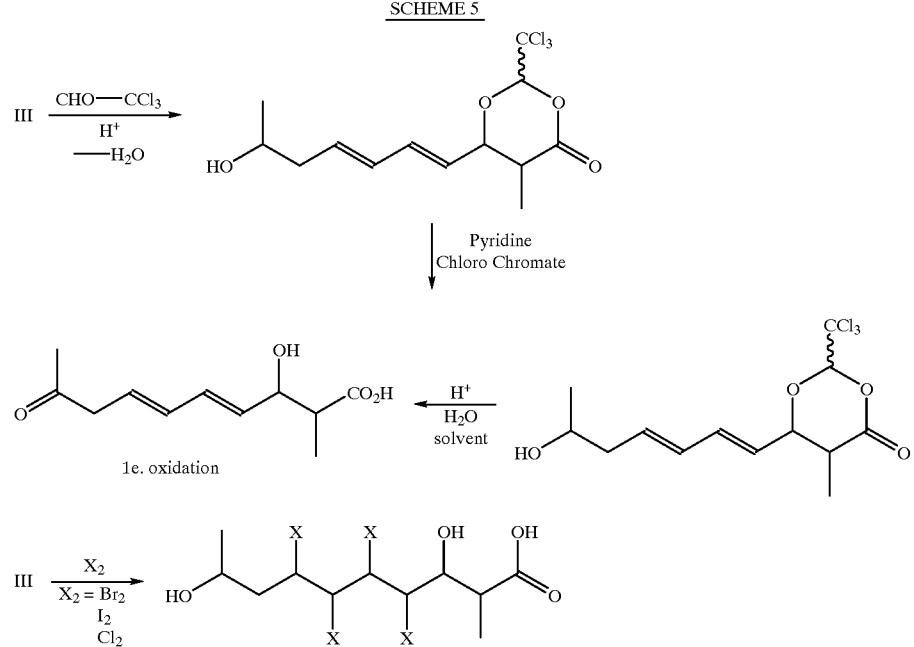

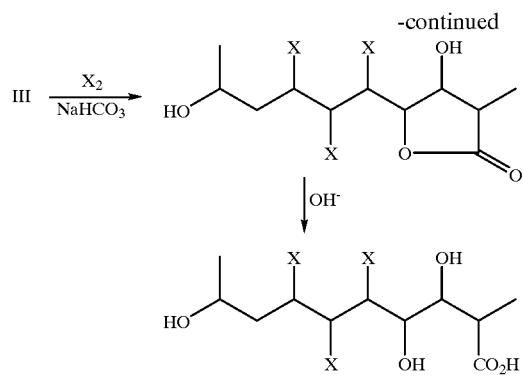
SCHEME 6
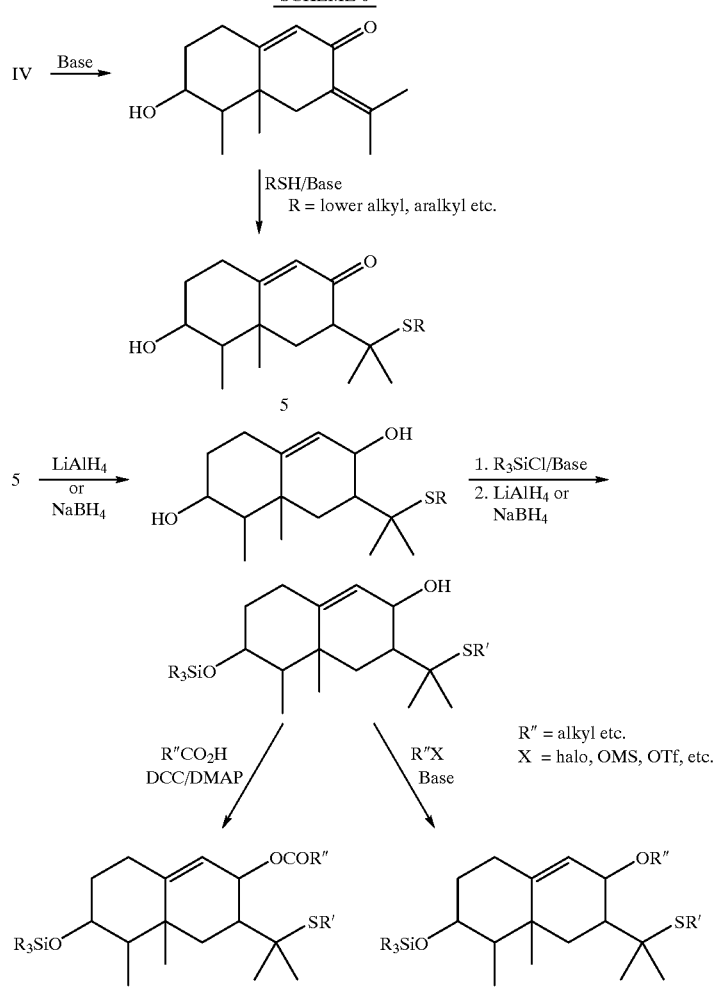

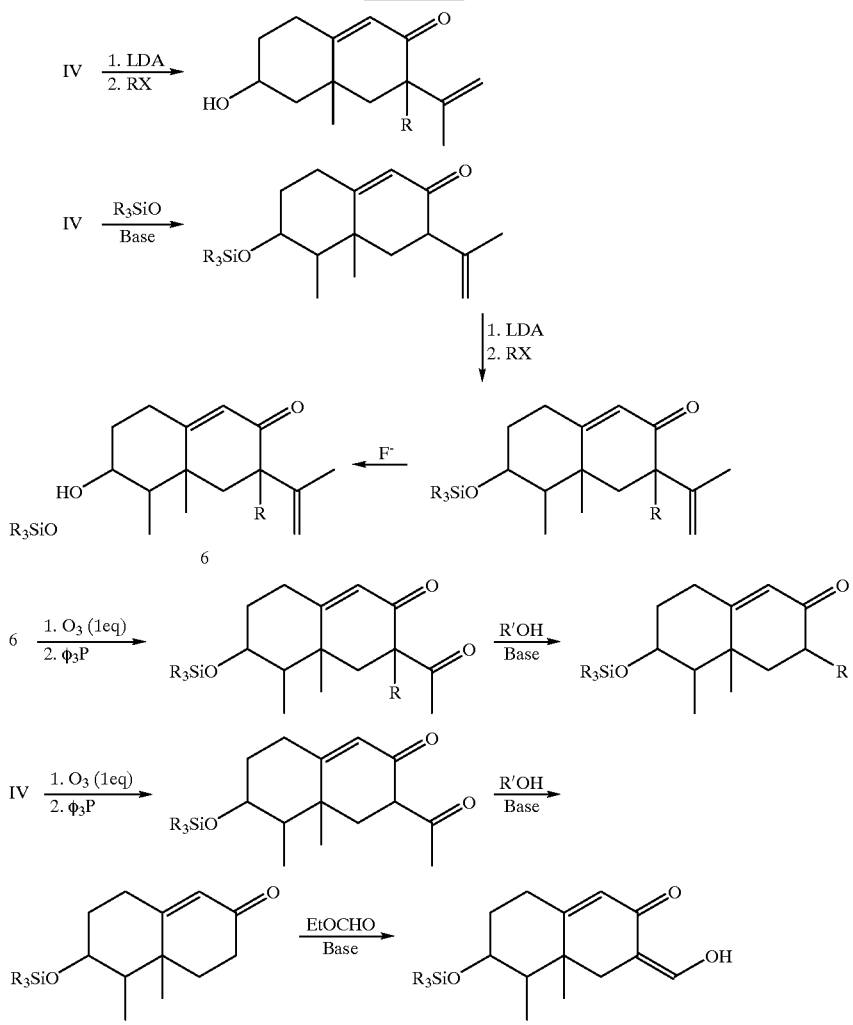
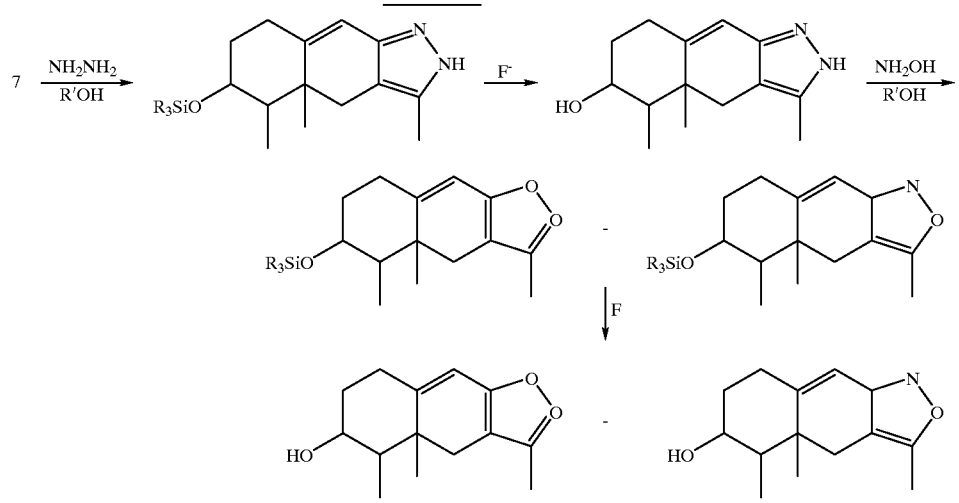

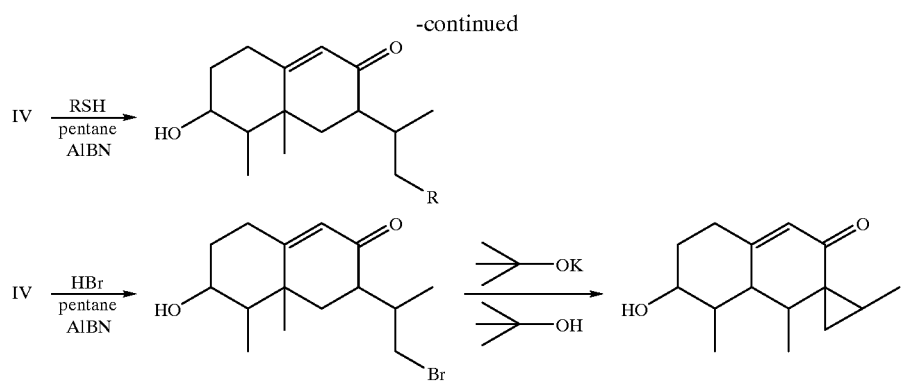
SCHEME 9
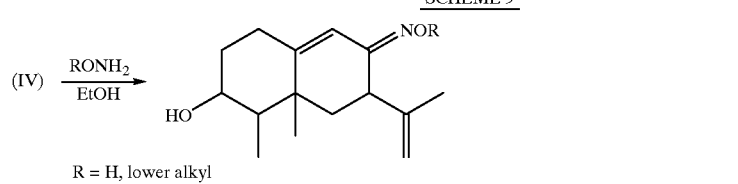
R = H, lower alkyl
Derivatization of cmpd 3390(11)
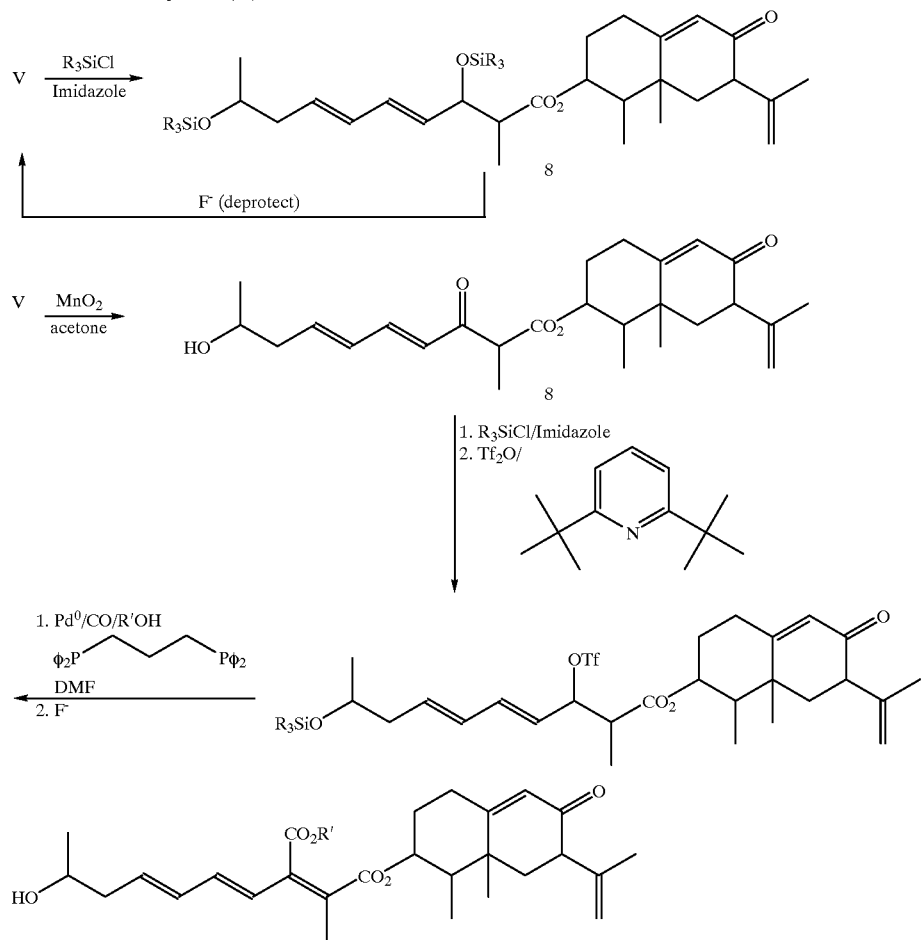

SCHEME 10
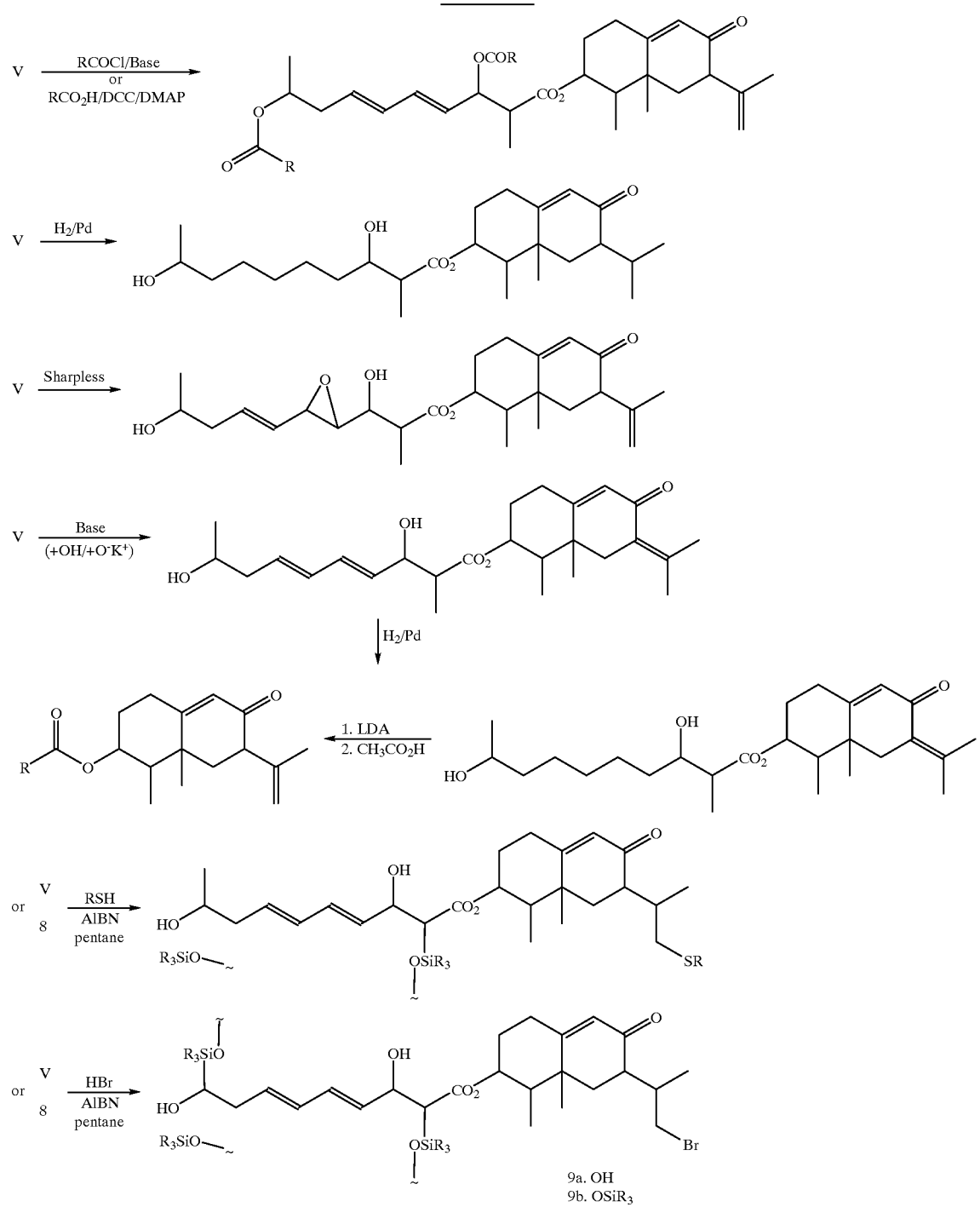

SCHEME 11
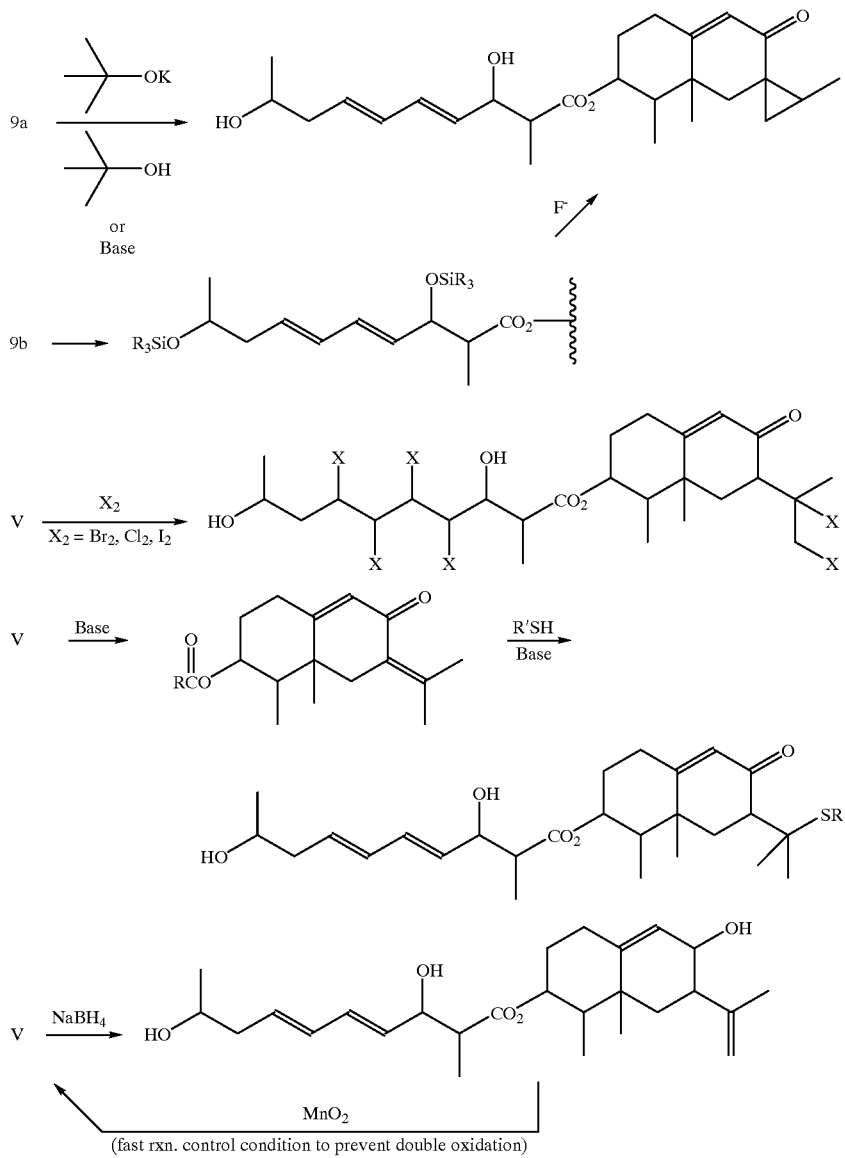
SCHEME 12
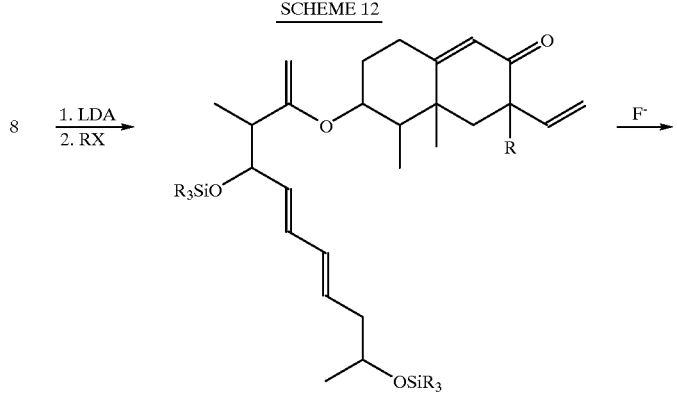

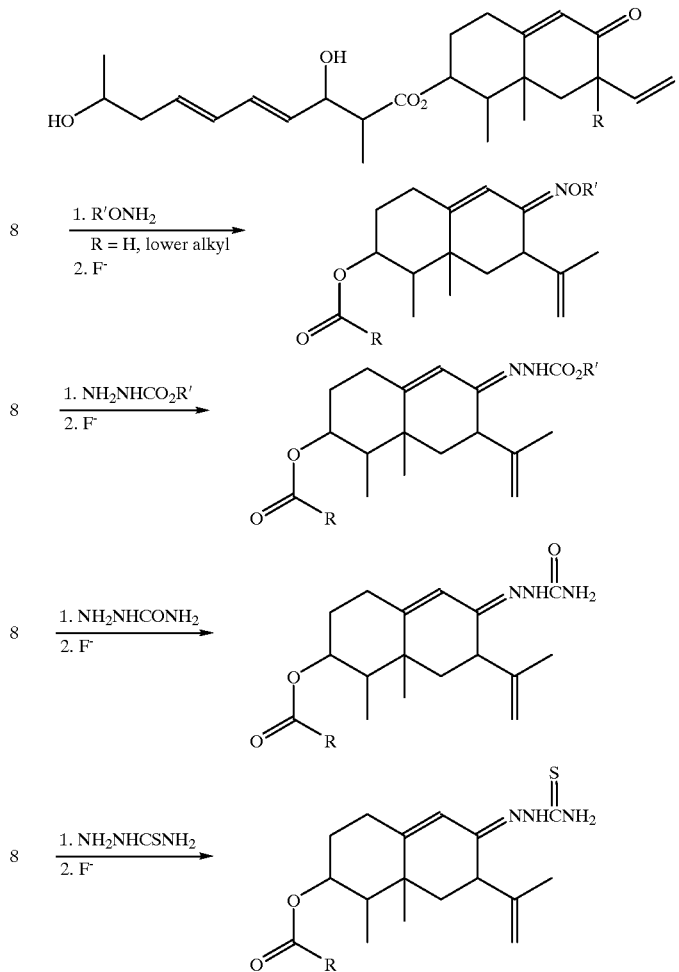

2. Protecting groups

Numerous thiol-, amino-, hydroxy- and carboxy-protecting groups are well-known to those in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in T. W. Greene and P. G. M. Wuts, *Protective Groups in Organic Chemistry*, (2nd ed., 1991).

The invention also encompasses isotopically-labelled counterparts of compounds disclosed herein. An isotopically-labelled compound of the invention has one or more atoms replaced with an isotope having a detectable particle- or x-ray-emitting (radioactive) nucleus or a magnetogyric nucleus. Examples of such nuclei include $^2H$, $^3H$, $^{13}C$, $^{15}N$, $^{19}F$, $^{29}Si$, $^{31}P$, $^{32}P$ and $^{125}I$. Isotopically-labelled compounds of the invention are particularly useful as probes or research tools for spectrometeric analyses, radioimmunoassays, binding assays based on γ- or β-scintillation, fluorography, autoradiography, and kinetic studies such as inhibition studies or determination of primary and secondary isotope effects.

3. Total Synthesis

In another aspect, the invention includes additional functional and structural analogs of the parent compound 3390. In this aspect, the conjugated diene skeleton can be replaced by isosteric monocyclic or bicyclic structures, or other $sp^2$-hybridized moieties such as carbonyls, amides, tertiary or secondary amines.

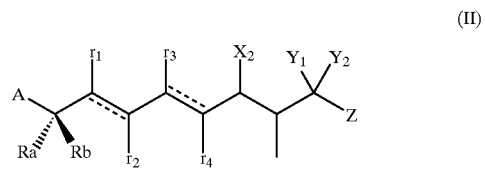

(II)

In formula (II) above, for example, each of $r_1$, $r_2$ $r_3$ and $r_4$ is selected independently from H, methyl, and halomethyl; or $r_1$ and $r_3$, or $r_2$ and $r_4$, taken together are a bivalent moiety which forms a $C_{3-20}$ substituted or unsubstituted five- or six-membered cycloalkyl, cycloalkenyl, aromatic, heterocyclic or heteroaromatic ring.

In this aspect, A includes any side chain of a naturally-occurring amino acid, $C_{2-10}$ hydroxy-alkyl, $C_{1-10}$ mercaptoalkyl, $C_{2-10}$ alkenylene, $X_1$(CH—)$R_1$, or $X_1$(C—)

$R_1$, wherein $X_1$ is H, F, Cl, Br, I, $C_{1-10}$ alkyl, $C_{2-10}$ alkenyl, $C_{2-10}$ alkenylene (where A is $X_1(C\!\!=\!\!)R_1$), $C_{1-10}$ haloalkyl, $OR_i$, $SR_i$, $NR_iR_{ii}$, or $NR_i(C\!\!=\!\!O)R_{ii}$, each of $R_i$ and $R_{ii}$ being independently selected from H, $C_{1-10}$ alkyl, and ($C_{6-14}$ aryl) ($C_{0-6}$ alkyl); and $R_1$ is H, $C_{1-6}$ alkyl, $C_{1-10}$ alkenyl, or =O (where A is $X_1(C\!\!=\!\!)R_i$). It will be easily apparent to those in the art that some categories of A overlap. Thus, to avoid redundancy within a single claim, it will be understood that where A is $X_1(C\!\!=\!\!)R_1$, either $R_1$ is =O or $X_1$ is $C_{2-10}$ alkenylene; and that where A is $X_1(CH\!\!=\!\!)R_1$, $X_1$ and $R_1$ are not such that A is a side chain of a naturally-occurring amino acid. Other variables are as described above in formula (I).

The invention also features a compound of the formula (VI). Based on the synthetic pathways provided in the disclosed schemes, the compounds of claim VI can be easily prepared from isolated natural products by one of ordinary skill in synethetic organic chemistry. In addition, the C-11 methylidene group can be oxidized to form a methyl ketone, a highly versatile moiety which allows chain extension by a variety of reactions. In formula (VI), Z is —(C=O)—NH—, —(C=O)—O—, —O—, —NH—(C=O)—, or —O—(C=O)—. As shown, the Z moieties have a specific orientation, where left-most valence, e.g., carbonyl carbon of the first amide bond (or the amino nitrogen of the second amide bond), is bonded to carbon atom attached to $r_a$ and $r_b$. In one embodiment of formula VI, one of $r_a$ and $r_b$ is methyl, one of $r_c$ and $r_d$ is hydroxyl, one of $r_e$ and $r_f$ is H, and one of $r_g$ and $r_h$ is hydroxyl and the other is methyl. In another embodiment, at least three of $r_a$–$r_h$ are hydroxyl and at least two of the remaining of $r_a$–$r_h$ are methyl. In other embodiments, X is H; X is not H; or Z is —(C=O)—NH—, —(C=O)—O—, or —O—.

E. Use

The disclosed compounds are useful to treat fungal infections. The methods of the invention contemplate treatment of animal subjects, such as mammals (e.g., higher primates, and especially humans), animal cell and tissue cultures, plants (e.g., food crops), and plant cell and tissue cultures. The invention encompasses pharmaceutical (or veterinary or agricultural) compositions which include compounds described herein.

Where the compound contains a basic group, pharmaceutically acceptable salts may be formed, for example, with 1, 2, 3, or more equivalents of hydrogen chloride, hydrogen bromide, trifluoroacetic acid, and others known to those in the art of drug formulation. Sodium, potassium, ammonium, calcium, aluminium, or magnesium salts can be prepared where the compound contains an acid group, using a hydroxide compound or other base. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-inflammatory, analgesic, or other agents. A compound of the invention may be administered in unit dosage form, and may be prepared by any of the methods well known in the pharmaceutical art, for example, as described in *Remington's Pharmaceutical Sciences* (Mack Pub. Co., Easton, Pa., 1980). The invention also encompasses a packaged drug, containing a pharmaceutical composition formulated into individual dosages and printed instructions for self-administration.

Compounds disclosed herein may also be formulated for topical or parenteral administration, particularly in the form of solutions or liquid suspensions; for oral administration, particularly in the form of tablets or capsules; or intranasally, particularly in the form of powders, gels, oily solutions, nasal drops, aerosols, or mists. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactideiglycolide or polyoxyethylene/polyoxypropylene. Additional parental delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 1–10% w/v of compound for parenteral administration. Typical dose ranges are from about 1–100 mg/kg of body weight per day, and preferably 2–10 mg/kg, given in 1–4 divided doses. Each divided dose may contain the same or different compounds of the invention. The dosage will be an effective amount depending on several factors including the overall health of a patient, and the formulation and route of administration of the selected compound(s).

The effective amount of the active compound used to practice the present invention for treatment of conditions directly or indirectly mediated by fungal infection varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount".

One aspect of the invention is a method of treating fungal infection in a patient (e.g., a mammal, e.g., a human, a mouse, a rat, or a cow), including administering to the patient an effective amount of a pharmaceutical composition containing an antifungal compound having a formula (I) or (VI); and a pharmaceutically acceptable carrier, thereby treating fungal infection in the patient. A pharmaceutical composition can include a plurality of antifungal or anticancer compounds, whether disclosed herein or otherwise known, in any beneficial proportion.

Other aspects of the invention include the use of disclosed compounds as laboratory reagents to promote tubulin polymerization and tubulin assembly and in diagnostic kits used to screen for compounds which promote or inhibit the formation of mammalian or fungal microtubules or to screen a cell sample for the presence or absence of an endogenous substance that is required for tubulin polymerization and tubulin assembly. The cell sample may be taken from the skin, a mucous membrane (inner mouth, gastrointestinal tract, urogenital tract), a subcutaneous biopsy, or biological fluids.

Without further elaboration, it is believed that one skilled in the art can, based on this disclosure, realize the present invention to its fullest extent. The following example is, therefore, merely illustrative. All publications cited herein are hereby incorporated by reference.

EXAMPLE 1

Microtubule destabilizing agents

The tubA4 mutation produces a strain more susceptible to microtubule destabilizing agents than wild type. The *A. nidulans* tubA4 strain produces yellow conidia; when mixed with wild type, green conidia are produced. A mixture of *Aspergillus nidulans* conidia from green TubA+ (wildtype) and yellow tubA4 mutant is surface-inoculated onto nutrient agar in standard 96 well microtiter plates. The ratio of green to yellow conidia is chosen such that after incubation, a well containing no test compound is predominantly yellow, whereas a well containing an appropriate concentration of a microtubule inhibitor such as Benomyl, is green.

Twenty microliters of a 1-butanol solution of Benomyl (two-fold serial dilution between 0.16 μg/ml and 5.0 μg/ml) are added to wells H1 to H6. After solvent was removed in a Savant Speedvac under reduced pressure (0.8 torr), 200 μl molten CM agar was added to each well. Two and one-half microliters of a conidial suspension of appropriate count and color ratio was applied to the surface of the solidified agar. After incubation with fluorescent lighting at 37° C. for 48 hours, the plates were scored. Variations range from solid green, green/yellow, solid yellow, yellow/trace of green, severe growth inhibition, and no pigment.

In the absence of test samples, the color was predominantly but not pure yellow. In the presence of a microtubule destabilizing agent, such as benomyl, the color was green. In the presence of some test substances, the cell mixture became completely yellow, indicating preferential inhibition of wild type growth. The presence of the tubA4 allele which encodes less stable microtubules therefore provides an advantage in the presence of an agent that stabilizes microtubule assembly, such as taxol. This assay identifies agents which stabilize microtubules. Formula V was shown to stabilize microtubules (see U.S. application Ser. No. 08/113, 264, now abandoned).

OTHER EMBODIMENTS

From the above description, the essential characteristics of the present invention can be easily ascertained. Without departing from the spirit and scope thereof, various changes and modifications of the invention can be made to adapt it to various usages and conditions. Thus, other embodiments are also within the claims.

What is claimed is:

1. A method of treating a fungal infection in a patient, comprising administering to the patient an effective amount of pharmaceutical composition comprising a compound having the formula (VI):

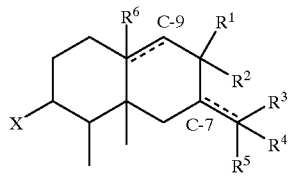

(VI)

wherein each of $R^1$ and $R^2$ is independently selected from H, $C_{1-10}$ alkyl, $C_{1-10}$ alkoxy, $C_{2-10}$ alkenyl, $C_{2-10}$ alkenoxy, $C_{6-10}$ aryl, substituted or unsubstituted $C_{6-10}$ alkylcarbonyloxy, and $C_{2-10}$ acyloxy; or $R^1$ and $R^2$ taken together are =O or substituted or unsubstituted $C_{1-10}$ alkylenedioxy, carbonyldioxy, and other carbonyl-protecting groups;

when there is no double bond between C-7 and C-11, each of $R^3$, $R^4$ and $R^5$ is independently selected from $C_{1-10}$ alkyl, $C_{1-10}$ alkoxy, and $C_{1-10}$ acyloxy; or $R^4$ and $R^5$ taken together are =O, $C_{1-10}$ alkylidene, or $C_{1-10}$ alkenylidene; and when there is a double bond between C-7 and C-11, $R^3$ and $R^4$ are independently selected from $C_{1-10}$ alkyl, $C_{1-10}$ alkoxy and $C_{1-10}$ acyloxy; and $R^5$ is absent;

$R^6$ is $C_{1-10}$ alkylamino or $C_{1-10}$ alkylthio when there is no double bond between C-9 and C-10; $R^6$ is absent when there is a double bond between C-9 and C-10;

X is H, OH, $OR_p$ where $R_p$ is $C_{1-10}$ alkyl, $C_{6-10}$ aryl, $C_{2-10}$ acyl, $C_{6-10}$ arylcarbonyl, tri($C_{1-6}$ alkyl)silyl, and other hydroxy-protecting groups, or Y having the formula:

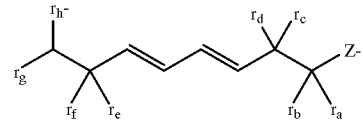

Z is —(C=O)—NH—, —(C=O)—O—, or —O—; and each of $r_a$–$r_h$ is independently selected from H, methyl, halomethyl, hydroxy, and $OR_p$, where $R_p$ is $C_{1-10}$ alkyl, $C_{6-10}$ aryl, $C_{2-10}$ acyl, $C_{6-10}$ arylcarbonyl, and other hydroxy-protecting groups, provided that at least two of $r_a$–$r_h$ are hydroxyl groups which do not form a gem-diol;

provided that where X is OH, —C($R^3$)($R^4$)($R^5$) is neither isopropenyl nor isopropylidene; where X is O-(trialkylsilyl), —C($R^3$)($R^4$)($R^5$) is not 2-hydroxyisopropyl; and provided that when $R^1$, $R^2$, and X are H, —C($R^3$)($R^4$)($R^5$) is not isopropenyl;

or a pharmaceutically acceptable salt thereof and a pharmaceutically-acceptable carrier, thereby treating said fungal infection.

2. A method of claim 1, wherein one of $r_a$ and $r_b$ is methyl, one of $r_c$ and $r_d$ is hydroxyl, one of $r_e$ and $r_f$ is H, and one of $r_g$ and $r_h$ is hydroxyl and the other is methyl.

3. A method of claim 1, wherein at least three of $r_a$–$r_h$ are hydroxyl and at least two of the remaining of $r_a$–$r_h$ are methyl.

4. A method of claim 1, wherein the patient is a mammal.

5. A method of claim 4, wherein the mammal is a human.

* * * * *